United States Patent
Garbagnati et al.

(10) Patent No.: US 6,623,481 B1
(45) Date of Patent: Sep. 23, 2003

(54) ELECTROSURGICAL PROBE FOR TUMOR TREATMENT BY RADIOFREQUENCY

(75) Inventors: Francesco Garbagnati, Milan (IT); Sandro Rossi, Piacenza (IT)

(73) Assignee: Thermo-Med 2000 KFT (HU)

( * ) Notice: Subject to any disclaimer, the term of this patent is extended or adjusted under 35 U.S.C. 154(b) by 0 days.

(21) Appl. No.: 10/031,621

(22) PCT Filed: Jul. 19, 2000

(86) PCT No.: PCT/IT00/00301
§ 371 (c)(1),
(2), (4) Date: Jan. 18, 2002

(87) PCT Pub. No.: WO01/05317
PCT Pub. Date: Jan. 25, 2001

(30) Foreign Application Priority Data

Jul. 21, 1999 (IT) .......................................... MI99A1608

(51) Int. Cl.[7] .............................................. A61B 18/14
(52) U.S. Cl. ........................................... 606/41; 606/49
(58) Field of Search ............................. 606/41, 48, 49, 606/50; 607/99

(56) References Cited

U.S. PATENT DOCUMENTS

| | | | | |
|---|---|---|---|---|
| 5,282,845 A | * | 2/1994 | Bush et al. ................. | 607/128 |
| 5,370,675 A | * | 12/1994 | Edwards et al. ............. | 607/101 |
| 5,683,384 A | * | 11/1997 | Gough et al. ................ | 606/41 |
| 5,741,225 A | | 4/1998 | Lax et al. | |
| 5,913,855 A | | 6/1999 | Gough et al. | |
| 6,235,023 B1 | * | 5/2001 | Lee et al. ................... | 606/41 |

FOREIGN PATENT DOCUMENTS

| | | | | |
|---|---|---|---|---|
| DE | 2124684 | * | 3/1971 | ............. 607/116 |
| WO | WO 99/44506 | | 9/1999 | |

* cited by examiner

*Primary Examiner*—Lee Cohen
*Assistant Examiner*—Aaron Roane
(74) *Attorney, Agent, or Firm*—Muserlian, Lucas and Mercanti, LLP

(57) ABSTRACT

An electrosurgical probe including a metal cannula, partially provided with an electroinsulating coating, and filiform electrodes housed in the cannula in a stretched position. The filiform electrodes are provided with an elastic memory of an arched shape and as a result, come out from the cannula to occupy a limited, nearly spherical volume. The electrodes are fixed to the distal end of a control rod slidably arranged inside the cannula so that the electrodes in a stretched position are arranged side by side parallel with the control rod. The cannula includes a series of holes each positioned immediately under the free ends of the filiform electrodes and having a sufficient diameter for the passage of a respective one of the electrodes. The electrodes are removed from the cannula by pulling the control rod and retracted into the cannula by pushing the control rod.

20 Claims, 1 Drawing Sheet

ELECTROSURGICAL PROBE FOR TUMOR TREATMENT BY RADIOFREQUENCY

This patent application claims a benefit of priority from Italian Patent Application No. MI99A001608 filed Jul. 21, 1999, through PCT Application Serial No. PCT/IT00/00301 filed Jul. 19, 2000, the contents of each of which are incorporated herein by reference.

FIELD OF THE INVENTION

The present invention relates to an electrosurgical probe for tumor treatment by radiofrequency energy, and particularly to a probe containing a plurality of needle-shaped electrodes whose tips can be expanded at the tumor to be treated so as to affect a volume of cancer tissue which is as large as possible.

BACKGROUND OF THE INVENTION

The tumor treatment by hyperthermia which is induced by radiofrequency energy or other energy forms is already known in medicine. Electrosurgical probes provided with needle-shaped electrodes which, by penetrating into the cancer tissue, cause its necrosis, have already been developed.

International Publication No. WO 96/29146 describes electrosurgical probes comprising independent needle-shaped electrodes which are pushed inside the tissue to be treated by making them come out from the point of a metal cannula inserted into the patient's body. This is obtained by using electrodes formed of thin metal wires having an arched end provided with elastic memory which is kept in a substantially stretched condition inside the cannula and is released, expanding itself, when the electrodes are pushed out of the cannula in order to penetrate into the tissue to be treated. An object of this expansion is that a volume of cancer tissue to be treated which is as large as possible is affected.

U.S. Pat. No. 5,813,855 and International Publication No. WO 98/52480 describe other electrosurgical probes which are also formed of a rigid cannula containing one or a plurality of filiform electrodes having arched tips with elastic memory which are compressed inside the cannula in a stretched position and which expand themselves when they are pushed out of the cannula inserted inside the tissue to be treated. The filiform electrodes are arranged inside the cannula around a central nucleon so that, when their tips are pushed out from the point of the cannula, the cancer tissue is affected in a regular volume which is as similar as possible to a sphere.

However, none of the presently known electrosurgical probes is capable of creating an electrical field having a real spherical shape, but rather, in the known electrosurgical probes, it is at the most possible to obtain an electrical field having an ellipsoidal shape since, as is apparent from FIGS. 4 and 5 of WO 98/52480, only a small portion of the distal end of the metal cannula which participates to the formation of the electrical field is surrounded by the arched ends of the filiform electrodes.

Another drawback of the known electrosurgical probes is that their use involves the risk that the arched ends of the electrodes, by penetrating into the cancer tissue under the impulse of the suitable control, may go beyond the appointed target and penetrate also in vital structures, for instance a blood vessel, adjacent to the portion to be treated.

OBJECTS AND SUMMARY OF THE INVENTION

Therefore, an object of the present invention is to provide an electrosurgical probe of the type with multiple needles having an arched point with elastic memory which is free from the above mentioned drawbacks.

This object is achieved by the electrosurgical probe having a cannula having a plurality of holes and a distal end and a proximal end and a plurality of filiform electrodes housed in the cannula and having an elastic memory of an arched shape. The number of electrodes corresponds to the number of holes in the cannula and each hole has a size to allow passage of a respective electrode therethrough. A control rod is movably arranged in the cannula and has a distal end and a proximal end. The electrodes are fixed to the distal end of the control rod and have a free end extending toward the proximal end of the cannula when housed therein. Each electrode is arranged to move rearward in the cannula to pass through a respective hole in the cannula and then to arch forward toward the distal end of the cannula upon pulling the proximal end of the control rod in a rearward direction. As such, the movement of the electrodes in the cannula and the direction of pulling of the control rod are in the same rearward direction.

The electrosurgical probe according to the present invention eliminates the first of the above mentioned drawbacks of the probes according to the prior art, because it has the important feature that the electrodes, when they are outside the cannula, are arranged like the meridians of an ideal sphere whose diameter is formed of a long segment of the cannula distal portion, which is not coated by the insulating material. Accordingly, also the cannula in its distal portion participates in creating the active field of the radiofrequency. As a matter of fact, when the needle-shaped electrodes protrude from the cannula, the arched portion of each electrode forms an arc of 180° whose two ends are located near to the two ends of the uncoated distal portion of the cannula, that is, near to the two poles of the ideal sphere of which that portion of the cannula forms the diameter.

The second of the above mentioned drawbacks of the known electrosurgical probes is eliminated by means of the probe according to the present invention because it has the feature that the expansion of the arched tips of the electrodes is controlled by traction of the electrodes and not by thrust like in the known probes. In other words, whereas in the known probes the expansion of the filiform electrodes is controlled by a movement in the same direction of penetration of the electrodes into the patient's tissues, in the probe according to the present invention, the expansion is controlled by traction, that is by a movement in the opposite direction with respect to that of penetration of the electrodes into the patient's tissues. As a result, the free end of each filiform electrode will have the tendency to converge, after the expansion movement, towards the distal end of the metal cannula, thus avoiding the risk that it may diverge towards vital structures and perforate them. This is due to the fact that in the probe according to the present invention, in the rest position thereof, both the filiform electrodes and the rod which controls them have the same direction but they are turned in different directions after the expansion.

Besides eliminating the above mentioned drawbacks of the probes according to the prior art, the electrosurgical probe according to the present invention offers another important advantage, that is preventing, during this operation, the electrodes from coming out accidentally from the probe point during the positioning operation of the probe itself into the tissue. This is due to the fact that the operation for causing the electrodes expansion takes place by retraction with a movement in the opposite direction with respect to the positioning movement, and not in the same direction like in the prior art.

A further advantage of the electrosurgical probe according to the present invention with respect to the prior art is that no free space between the distal end of the cannula and the content thereof is provided. As a matter of fact, this free space, which is present in the known probes, may cause undesired phenomena of core boring of healthy tissue of the patient during the probe positioning operation. The structure of the probe according to the present invention allows also to close the distal end of the cannula and to confer it a pointed tip.

BRIEF DESCRIPTION OF THE DRAWINGS

These and other advantages of the electrosurgical probe according to the present invention will be evident to those skilled in the art from the following detailed description of one embodiment thereof with reference to the accompanying drawings, wherein.

DETAILED DESCRIPTION OF THE INVENTION

Figure 1:
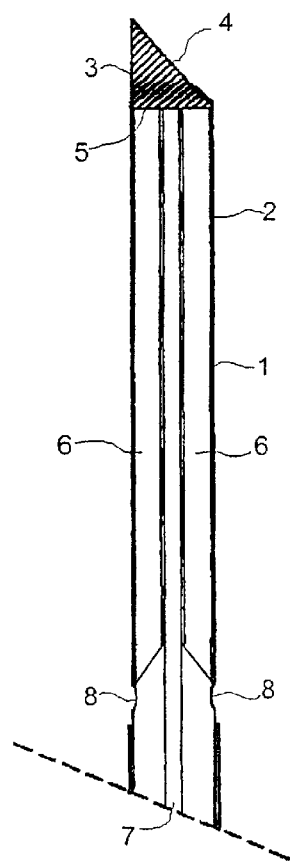
FIG. 1 shows an enlarged and partially sectioned view in side elevation of the cannula of the probe according to the present invention.

With reference to FIG. 1, there is shown that the electrosurgical probe according to the present invention comprises a metal cannula 1, of a known kind, inside which a head 3 is placed, having the upper end 4 preferably pointed like a flute mouthpiece. Also the point of cannula 1 can be pointed like a flute mouthpiece like the upper end 4 of head 3. In this way, the point of head 3 can coincide in the rest position with the point of cannula 1 without any free space between the two points. This structural measure avoids the undesirable phenomena of core boring of healthy parenchymatous tissue which occur by using the probes according to the prior art wherein a free space between the piston head which pushes the electrodes and the point of the cannula which contains them necessarily exists.

It is obvious that the point of head 3 in the rest position can also protrude from the end 2 of the cannula 1, because this is open. However, constructive variants are possible, with a closed and sharp point of cannula 1, or with an open cannula 1 and a pointed head 3 like in FIG. 2. Other embodiments are obviously possible in order to fix the base of the electrodes to the distal end of their control rod so that in the stretched position they are side by side with the axis.

From base 5 of head 3, a plurality of filiform electrodes 6, as well as control rod 7 of head 3, branch off downwards. This is the most innovative and advantageous feature of the electrosurgical probe according to the present invention, with respect to that of the prior art wherein the electrodes in the stretched position form the prolongation of the electrode control rod and are not at the side thereof. The filiform electrodes 6 having elastic memory of shape are already known in the art and therefore they do not need a detailed description.

The filiform electrodes 6 are arranged on the side and parallel to rod 7 in a stretched position with their downward turned tips which are near or slightly above a multiplicity of holes 8 arranged along the circumference of cannula 1. The number of holes 8 corresponds to the number of electrodes 6 so that each electrode 6 has a relevant hole 8 for coming out of cannula 1 when rod 7 of head 3 is pulled downwards. Holes 8 are arranged such that each of the electrode points can pass through the relevant hole 8 in order to get out of cannula 1 under the thrust of head 3 when the head 3 is pulled downwards. As soon as rod 7 is pulled downwards, electrodes 6 come out of holes 8 of cannula 1, gradually regaining their naturally arched shape by virtue of their elastic memory, thus assuming in the end the configuration shown in FIG. 2.

Figure 2:
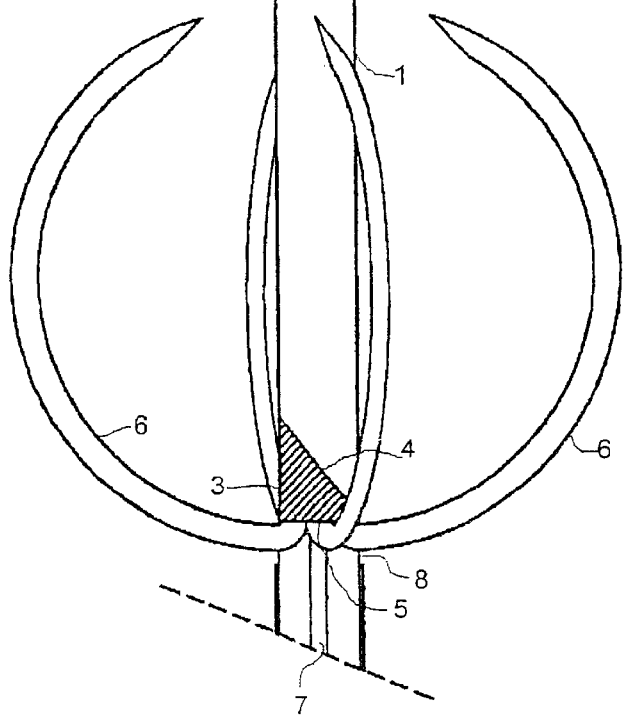
FIG. 2 shows a similar view of the same cannula of FIG. 1, but with the arched tips of the electrodes taken out from the cannula and in the working position.

With reference to FIG. 2, there is shown that each electrode 6, after passing through the relevant hole 8, under the thrust of head 3 which is pulled downwards by means of control rod 7, has passed nearly completely through the relevant holes 8, thus penetrating in the cancer tissue to be treated or surrounding it. In the course of the penetration, by virtue of the elastic memory of which filiform electrodes 6 are provided, these expand themselves while bending until they assume the position shown in FIG. 2. As it can be seen, each electrode 6 has assumed a position which greatly resembles that of a meridian of an ideal sphere. This shape is much more regular than those which can be obtained by the electrosurgical probes according to the prior art. This regularity depends substantially on the fact that filiform electrodes 6 are not only pushed inside the cancerous tissue, like in the known electrosurgical probes, but they are also guided from the lower ends of the relevant holes 8 suitably provided along the circumference of cannula 1.

Holes 8 can have any suitable shape for favoring the coming out of the needle-shaped electrodes and for guiding them upwards as soon as they come out from cannula 1. The preferred shape for holes 8 is the one slightly lengthened in the direction of the length of the needle-shaped electrode so as to favor the coming out thereof from cannula 1. The lower rim of the hole is provided with a profiled upward-turned cross-section which forms an upward-directed guide plane for the needle-shaped electrode which helps it in its expansion until it reaches the position shown in FIG. 2.

Obviously, the number of the holes depends on the number of the filiform electrodes. Their number varies according to the needs and can vary between two and twenty. In the embodiment shown in FIGS. 1–3, there are four. When the number of the filiform electrodes is very high, it is preferable that holes 8 are not circumferentially aligned on the surface of cannula 1, but arranged according to an elicoidal line or on more parallel circumferences.

Cannula 1 is provided with an insulating coating of a plastic material whose upper edge is positioned slightly under the last of holes 8. In this way, the exposed portion of metal cannula 1 during working forms the diameter of the ideal sphere created by the envelope of the needle-shaped electrodes.

Figure 3:
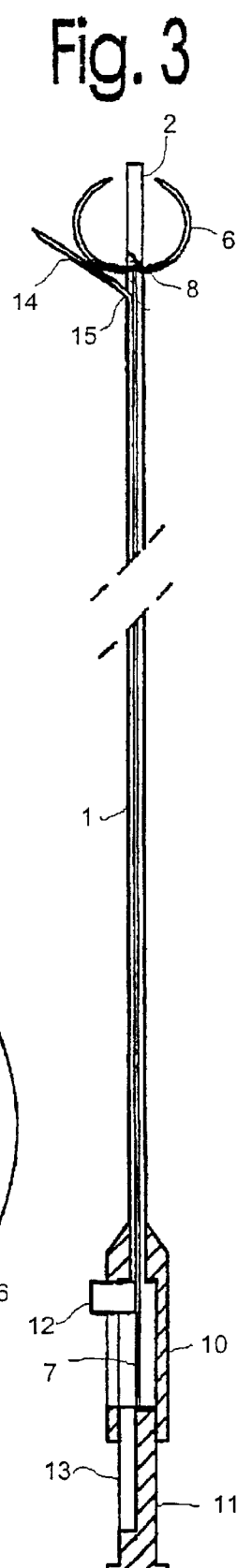
FIG. 3 shows a view in scale of a complete electrosurgical probe with the electrodes in the working position.

With reference to FIG. 3, there is shown an electrosurgical probe according to the present invention in the working position. In this position, the filiform electrodes 6 are already expanded and their points have reached a position very close to the distal end 2 of cannula 1. The coming out of electrodes 6 from the inside of cannula 2 has been caused by moving away head 3 from distal end 2 of the cannula 2. This movement away has been achieved by pulling control rod 7 by means of knob 9 which is thus progressively removed from handle 10 which is internally provided with a space suitable for housing stem 11 of knob 9. Handle 10 is also referred to as a knob herein.

In FIG. 3, there is also shown the independent lateral needle 14 which works as a support for one or more thermistors of the telethermometric system applicable to the probe according to the present invention. Needle 14 comes out of cannula 1 through a suitable hole 15 made on the cannula and is controlled by cursor 12 which is partially housed inside knob 10. In addition to lateral needle 14, the probe according to the present invention can be provided with one or more similar needles. Each one of needles 14 carrying thermistors can be rendered radiofrequency active at discretion, thus enlarging the extent of the thermolesion. In view of the presence of the cursor 12, the stem 11 of the knob 9 includes a slot 13 which allows movement of the cursor 12.

Obviously, the probe according to the present invention can be completed with the necessary connections to the radiofrequency generator and with all the other attachments necessary for its working, maintenance and use, as well as for the telethermometric check of the thermal lesion during the treatment.

In a preferred embodiment of the present invention, a thermistor has been applied on each end of the non-insulated portion of cannula 1. A third thermistor has been advantageously applied also on the insulated portion of cannula 1, immediately under holes 8.

Rigid cannula 1 can be replaced by a flexible tube in a portion comprised between the line of the holes 8 and handle 10. This embodiment allows the probe to be used as a catheter.

What is claimed is:

1. An electrosurgical probe, comprising:
   a cannula having a plurality of holes and a distal end and a proximal end;
   a plurality of filiform electrodes housed in said cannula and having an elastic memory of an arched shape, the number of said electrodes corresponding to the number of said holes in said cannula and each of said holes having a size to allow passage of a respective one of said electrodes therethrough; and
   a control rod movably arranged in said cannula and having a distal end and a proximal end, said electrodes being fixed to said distal end of said control rod and having a free end extending toward said proximal end of said cannula when housed in said cannula, each of said electrodes being arranged to move rearward in said cannula to pass through a respective one of said holes in said cannula and then to arch forward toward said distal end of said cannula upon pulling said proximal end of said control rod in a rearward direction such that the movement of said electrodes in said cannula and the direction of pulling of said control rod are in the same rearward direction.

2. The electrosurgical probe of claim 1, wherein said electrodes are arranged alongside one another when housed in said cannula.

3. The electrosurgical probe of claim 2, wherein said electrodes are arranged parallel to said control rod when housed in said cannula and said free ends of said electrodes are in alignment with said holes.

4. The electrosurgical probe of claim 1, wherein said electrodes are arranged parallel to said control rod when housed in said cannula.

5. The electrosurgical probe of claim 1, wherein said electrodes are arranged to extend along a meridian of a sphere having a center inside said cannula when outside of said cannula.

6. The electrosurgical probe of claim 1, wherein said electrodes are retracted into said cannula upon pushing said control rod in a forward direction.

7. The electrosurgical probe of claim 1, wherein said cannula is metal and at least partially coated with an electroinsulating coating.

8. The electrosurgical probe of claim 7, wherein said coating extends along said cannula up to said holes such that a portion of said cannula extending from said distal end of said cannula to said holes and including said holes is uncoated.

9. The electrosurgical probe of claim 1, further comprising a head mounted at said distal end of said control rod, said electrodes being fixed to a proximal surface of said head.

10. The electrosurgical probe of claim 1, further comprising a control knob arranged at said proximal end of said control rod for enabling pulling and pushing of said control rod.

11. The electrosurgical probe of claim 10, wherein said cannula has a hollow handle and said control knob has a stem coupling said control knob to said control rod, said control rod and said stem being arranged at least partially in said hollow handle of said cannula.

12. The electrosurgical probe of claim 1, wherein said cannula has a hollow handle, said control rod being arranged at least partially in said hollow handle of said cannula.

13. The electrosurgical probe of claim 1, wherein the number of said holes may be from one to twenty.

14. The electrosurgical probe of claim 1, further comprising at least one needle housed in and slidable outward from said cannula, said cannula having at least one additional hole through which a respective one of said at least one needle passes when slid outward from said cannula.

15. The electrosurgical probe of claim 14, further comprising a thermistor arranged at a tip of said at least one needle.

16. The electrosurgical probe of claim 14, wherein each of said at least one needle is arranged to be radiofrequency active.

17. The electrosurgical probe of claim 1, wherein said cannula has a handle arranged at said proximal end, said cannula being made of a rigid material between said handle and said holes.

18. The electrosurgical probe of claim 1, wherein said cannula has a handle arranged at said proximal end, said cannula being made of a flexible material between said handle and said holes.

19. An electrosurgical probe, comprising:
   a cannula having a plurality of holes and a distal end and a proximal end;
   a plurality of filiform electrodes having an elastic memory of an arched shape, the number of said electrodes corresponding to the number of said holes in said cannula and each of said holes having a size to allow passage of a respective one of said electrodes therethrough, said holes being arranged more proximate said proximal end of said cannula than said electrodes when said electrodes are housed in said cannula, said electrodes having a first position housed in said cannula between said distal end of said cannula and said holes and a second position outside of said cannula arched from a respective one of said holes toward said distal end of said cannula; and
   a control rod movably arranged in said cannula and having a distal end and a proximal end, said electrodes being fixed to said distal end of said control rod and having a free end extending toward said proximal end of said cannula when in said first position, said control rod being arranged to move said electrodes between said first and second positions whereby when said electrodes are moved from said first position to said second position, said electrodes are moved rearward and pass through the respective one of said holes in said cannula.

20. The electrosurgical probe of claim 19, wherein said electrodes are moved in a rearward direction within said cannula upon pulling said control rod rearward and retracted into said cannula upon pushing said control rod in a forward direction.

* * * * *